(12) United States Patent
Selig et al.

(10) Patent No.: US 8,900,226 B2
(45) Date of Patent: Dec. 2, 2014

(54) HF SURGICAL DEVICE

(75) Inventors: Peter Selig, Hechingen (DE); Martin Fritz, Tuebingen (DE)

(73) Assignee: ERBE Electromedizin GmbH, Tuebingen (DE)

( * ) Notice: Subject to any disclaimer, the term of this patent is extended or adjusted under 35 U.S.C. 154(b) by 451 days.

(21) Appl. No.: 13/394,391

(22) PCT Filed: Aug. 12, 2010

(86) PCT No.: PCT/EP2010/004953
§ 371 (c)(1),
(2), (4) Date: Mar. 6, 2012

(87) PCT Pub. No.: WO2011/029509
PCT Pub. Date: Mar. 17, 2011

(65) Prior Publication Data
US 2012/0165817 A1    Jun. 28, 2012

(30) Foreign Application Priority Data

Sep. 11, 2009 (DE) .......................... 10 2009 041 169
Oct. 13, 2009 (DE) .......................... 10 2009 049 180

(51) Int. Cl.
| | |
|---|---|
| A61B 18/12 | (2006.01) |
| A61B 5/00 | (2006.01) |
| A61B 18/00 | (2006.01) |
| A61B 5/053 | (2006.01) |

(52) U.S. Cl.
CPC ..... *A61B 5/6885* (2013.01); *A61B 2018/00702* (2013.01); *A61B 5/053* (2013.01); *A61B 2018/00875* (2013.01); *A61B 18/1206* (2013.01)

USPC .............................................. 606/38; 606/42

(58) Field of Classification Search
USPC ...................................................... 606/20–52
See application file for complete search history.

(56) References Cited

U.S. PATENT DOCUMENTS

| | | | |
|---|---|---|---|
| 6,186,147 | B1 | 2/2001 | Cobb |
| 6,203,541 | B1 | 3/2001 | Keppel |
| 2004/0097915 | A1 | 5/2004 | Refior et al. |

FOREIGN PATENT DOCUMENTS

| | | |
|---|---|---|
| EP | 1 051 948 A2 | 11/2000 |
| EP | 1 803 410 A1 | 7/2007 |
| JP | 2006-506172 A | 2/2006 |

*Primary Examiner* — Scott Getzow
(74) *Attorney, Agent, or Firm* — Dickstein Shapiro LLP

(57) ABSTRACT

An HF surgical device with an autostart function for cutting and/or coagulating biological tissue with HF current. The device comprises an HF generator for generating HF current, a selected output for connecting a monopolar/bipolar electrode to the HF surgical device, a first measurement device assigned to the output for measuring a first measured value for an impedance of the electrode connected to the output, a first comparator for comparing the first measured value with a first setpoint, for switching-off the first measurement devices and for switching-on a second measurement device if the first measured value is lower than the first setpoint, for measuring a second measured value for the impedance of the connected electrode and a second comparator for comparing the second measured value with a second setpoint and for switching-on the HF current for the output if the second measured value is lower than the second setpoint.

34 Claims, 5 Drawing Sheets

HF SURGICAL DEVICE

FIELD OF THE INVENTION

Embodiments of the invention relate to an HF surgical device with an automatic start function for cutting and/or coagulation of biological tissue and a method for the automatic starting of an HF current of an HF surgical device.

BACKGROUND

HF surgical devices with an automatic start function exist, where the HF current is activated with the pre-set parameters as soon as there is sufficient contact between the instrument and the tissue. This is possible for both bipolar and monopolar applications. The device can be configured such that the HF current is activated automatically when the tissue is touched with forceps or a clamp and the impedance then falls below a pre-set impedance threshold (after a defined time lag has elapsed).

The systems known to date have two disadvantages with the above method: as a rule, the devices either have a separate sensor system for determining the impedance between the terminals, or the measurement technology of the HF generator, which normally serves to establish the current HF operating data, is used for this function in combination with an HF generator as a source of measuring current.

If the latter is the case, then the HF generator is continuously activated with minimal voltage and current values, is switched to the outputs and the HF signal is used as a measurement parameter for the impedance. The advantage of this technique is that the measurement technology of the HF generator typically enables very precise measurements, but the serious disadvantage is that the measurement signals have relatively large voltage amplitudes of some tens of volts as a result of the design. This results in a continuous potential interference with sensitive devices in the vicinity, such as ECG monitors.

Moreover, autostart functionality can only be enabled at a single output of the device, since if a plurality of outputs are arranged in parallel then it is not possible to determine which output contributes the decisive part of the total impedance. It is not possible to rapidly switch the signal between different outputs because of the relay to be switched.

If, however, a separate sensor system is used for the autostart functionality (see, for example, EP 1051948 B1), then the amplitude of the measurement signals can be kept substantially lower. However, in addition to the measurement technology of the HF generator, a further very precise sensor system is necessary for monitoring the impedance at the output. In principle, this can be realized at a plurality of outputs in parallel, allowing the function to be selected at a plurality of outputs at the same time. This is, however, expensive and not favorable economically due to the required accuracy of the sensor system.

SUMMARY

An object of the embodiments of the invention is to provide an HF surgical device of the aforementioned type which, in an inexpensive manner on the one hand, enables an automatic start function at a plurality of terminals at the same time and, on the other hand, enables a precise determination of contact between electrode and tissue.

A substantial aspect of the disclosed embodiments of the invention is that after determining contact between tissue and an electrode with the aid of first measurement devices assigned to each output, the determination of the contact between tissue and electrode is checked with a second measurement device; the HF current for the corresponding output is only switched on once contact between the tissue and electrode has been confirmed by the second measurement device. This enables the first measurement devices to be less expensive than the second measurement device since, if the first measurement devices yield an imprecise/incorrect measurement, the current will not be switched on because of the second measurement process using the second measurement device.

In one embodiment, the second measurement device establishes a more precise measured value for the impedance of the electrode connected to the chosen output than the first measurement device. This has the advantage that the first measurement device can be very much simpler than the second measurement device.

The first measurement devices can use a lower voltage for the measurement of the impedance than the second measurement device. This reduces interference with other devices in the proximity of the HF surgical device due to electromagnetic radiation, voltage drops/peaks in the line network or the measurement current itself.

In a further embodiment, the HF surgical device has a third comparator for comparing the second measured value with a third setpoint and for switching off the HF current and the second measurement device, and for switching on the first measurement device if the second measured value is greater than or equal to the third setpoint. This allows the electrode connected to the chosen output to be provided with HF current until such time as contact with the tissue ceases; thus, the second measured value is greater than or equal to the third setpoint. The HF surgical device is then returned to its basic position.

The HF surgical device can have a fourth comparator for comparing the second measured value with a fourth setpoint and for switching off the second measurement device and turning on the first measurement device if the second measured value is greater than or equal to the fourth setpoint. One advantage of this is that the second measured value can be measured again as long as the second measured value is greater than or equal to the second setpoint and lower than the fourth setpoint i.e., if it is unclear whether the electrode was in contact with the tissue for only a short period of time or was only lightly touched by the electrode.

The third and fourth setpoints can have the same value. This simplifies the comparison of the second measured value with the third/fourth setpoint, and the threshold at which the HF surgical device is returned to its basic position is independent of whether the second measured value lay below the second setpoint or not.

In a further embodiment, the first measurement devices are configured such that they measure the first measured values at time intervals that are disjoint relative to one another. This largely prevents interference between the measurement devices due to cross-currents between the electrodes.

The second measurement device can be arranged in the HF generator to generate the HF current. This enables the connection paths between the second measurement device and the HF generator to be largely minimized. Furthermore, the second measurement device can be used to monitor the HF operating data.

A method, according to embodiments of the invention, for automatically starting an HF current of an HF surgical device comprises switching-on a first measurement device assigned to the output, measuring a first measured value for an impedance of the electrode connected to the output by the first measurement device, comparing the first measured value with a previously determined first setpoint, switching-off the first measurement devices and switching-on a second measurement device for the output if the first measured value is lower than the previously determined first setpoint, measuring a second measured value for the impedance of the electrode connected to the output by the second measurement device, comparing the second measured value to a second setpoint and switching-on the HF current for the output if the second measured value is lower than the previously determined second setpoint.

A further method, according to the embodiments of the invention, for the automatic starting of an HF current of an HF surgical device comprises the switching-on of a first measurement device assigned to the respective output, measuring a respective first measured value for an impedance of the electrode connected to the corresponding output by the first measurement devices, comparing the first measured value with a previously determined first setpoint, selecting an output at which the first measured value as the earliest in time of the first measured values is lower than the previously determined first setpoint, switching-off the first measurement devices and switching-on a second measurement device for the selected output, measuring a second measured value for the impedance of the electrode connected to the selected output by the second measurement device, comparing the second measured value with a second setpoint and switching-on the HF current for the selected output if the second measured value is lower than the previously determined second setpoint.

BRIEF DESCRIPTION OF THE DRAWINGS

Hereinafter, exemplary embodiments of the invention are explained in greater detail with reference to drawings, in which.

DETAILED DESCRIPTION

The same reference numbers are used for parts which are the same and for parts which have the same effect in the following description.

Figure 1:
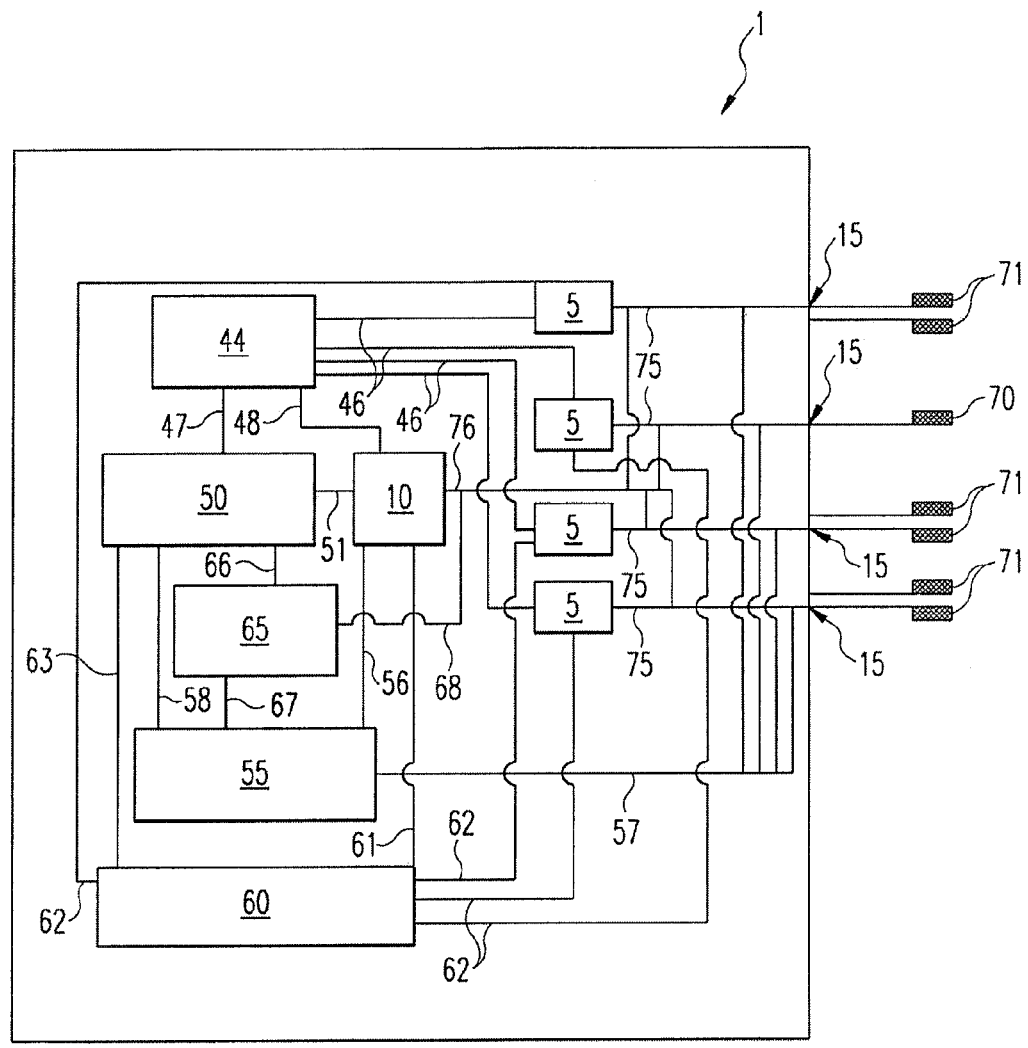
FIG. 1 is a schematic view of a circuit for a HF surgical device.
Figure 2:
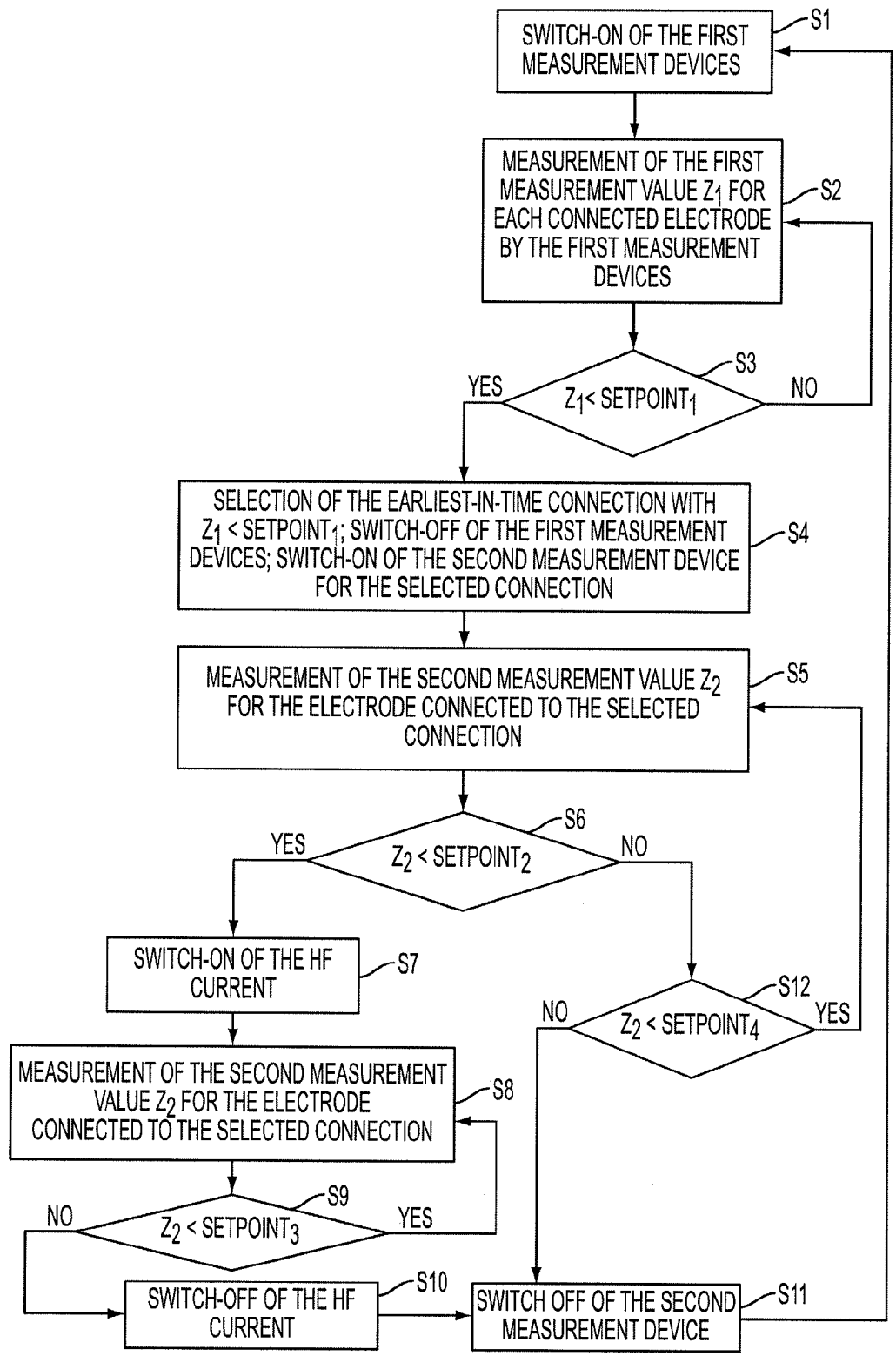
FIG. 2 is a flow diagram for operation of a HF surgical device with autostart function.

FIG. 1 is a schematic view of a circuit 1 for an HF surgical device with an autostart function. FIG. 2 is a flow diagram for a method for operating an HF surgical device with the autostart function. Circuit 1 has an HF generator 65 for generating the HF current. A first comparator 44, a second comparator 50, a third comparator 55 and a fourth comparator 60 are provided in the circuit 1. The circuit 1 has four outputs 15, to each of which either a monopolar electrode 70 or a bipolar electrode 71 is connected. A first measurement device 5 is assigned to each connection 15.

The autostart function is first activated for one or more outputs 15 by switching-on the respective first measurement device(s) 5 of an output 15 or a plurality of outputs 15 (block S1). The autostart function can be activated for all outputs 15 or for just some of the outputs 15 of the HF surgical device. The respective first measurement device 5, after the switch-on of the first measurement devices 5, measures via connecting lines 75 a first measured value $Z_1$ for the impedance of the respective electrode 70, 71 connected to the output 15, i.e., the impedance between the poles of the respective output 15 (block S2).

The impedance of the electrode 70, 71 connected to the output 15 is in general a complex valued; it can, however, also have just a real component or just an imaginary component, and/or only the real component or the imaginary component is measured. A person skilled in the art will be aware of different methods for measuring the impedance of an electrode 70, 71 or the impedance between two poles of an electrode. The first measurement devices can alternatively measure a different physical parameter of the corresponding electrode 70, 71 instead of the impedance.

Measurement of the first measured values may be at time intervals that are disjoint relative to one another. This allows interference between the first measurement devices 5 as a result of cross-currents to be largely reduced.

The first comparator 44 is connected via connection lines 46 to the first measurement devices 5 and compares the first measured value $Z_1$ to a first setpoint Setpoint$_1$ (block S3). If the first measured value $Z_1$ is equal to or greater than the first setpoint Setpoint$_1$, then it is assumed that no electrode 70, 71 has contacted tissue and the first measurement device 5 again measures (at block S2) a first measured value $Z_1$ for the impedance of the electrode 70, 71 at the respective output 15.

The first setpoint Setpoint$_1$ can be different for some of the outputs 15 or for each output 15. A different first setpoint Setpoint$_1$ can be assigned to each output 15, for example depending on the instrument connected or to be connected. In this case, the first comparator 44 compares the first measured value $Z_1$ for the respective output 15 to the first setpoint Setpoint$_1$ assigned to the corresponding output 15.

If the first measured value $Z_1$ is lower than the first setpoint Setpoint$_1$ (at block S3), then the first comparator 44 switches off the first measurement devices 5 of the outputs 15 and selects the output 15 corresponding to the earliest-in-time first measured value that is lower than the previously determined first setpoint Setpoint$_1$ (block S4). The first comparator 44 switches-on a second measurement device 10 of the HF surgical device for the selected output 15 via a connecting line 48 (also at block S4). The second measurement device is connected to each of the outputs 15 via a connecting line 76. The second measurement device 10 then measures a second measured value $Z_2$ for impedance of the electrode 70, 71 connected to the selected output 15 (block S5).

The second measurement device 10 may be a higher-quality measurement device than the first measurement devices 5. The second measurement device 10 can consequently establish a more precise measured value for impedance of the electrode 70, 71 connected to the selected output 15 than the respective first measurement device 5. To determine the impedance of the electrode 70, 71 connected to the selected output 15 more precisely, the second measurement device 10 uses a higher voltage than the first measurement devices 5. The use of a lower voltage for the measurement of the first measured value by the first measurement devices 5 results in a marked reduction in interference with other devices by the HF surgical device, since a higher voltage (e.g., some tens of volts) is used for a more precise measurement of impedance of the electrode 70, 71 connected to the selected output 15 only after tissue contact has been established by the first comparator 50.

The second comparator 50 is connected via a connecting line 51 to the second measurement device 10 and via a connecting line 63 to the fourth comparator 60. The second comparator 50 now compares the second measured value to a second setpoint (block S6). If the second measured value $Z_2$ is equal to or greater than the second setpoint $Setpoint_2$, then the fourth comparator 60, which is connected via connecting lines 62 to the first measurement devices 5, compares the second measured value to a fourth setpoint $Setpoint_4$ (block S12).

If the second measured value $Z_2$ is lower than the fourth setpoint $Setpoint_4$, then the second measured value $Z_2$ for the impedance of the electrode 70, 71 connected to the selected output 15 is measured again (at block S5) by the second measurement device 10. In this case, it is assumed that contact with the tissue was for only a short period or only slight.

If the fourth comparator 60 establishes, upon comparison, that the second measured value $Z_2$ is greater than or equal to the fourth setpoint $Setpoint_4$, then the fourth comparator 60 switches off the second measurement device 10 via a connecting line 61 and switches on the first measurement devices 5 (block S11). The circuit 1 of the HF surgical device is now returned to its basic state.

If during comparison of the second measured value $Z_2$ with the second setpoint $Setpoint_2$ (block S6), the second comparator 50 establishes that the second measured value is lower than the second setpoint $Setpoint_2$, then the second comparator 50, which is connected via a connecting line 66 to the HF generator 65, switches on the HF current for the selected output 15 (block S7).

After the HF current is switched on, the second measurement device 10 again measures the second measured value $Z_2$ for the impedance of the electrode 70, 71 connected to the selected output 15 (block S8). The third comparator 55, which is connected via a connecting line 56 to the second measurement device 10 and via connecting lines 57 to the outputs 15, compares the second measured value $Z_2$ to a third setpoint $Setpoint_3$ (block S9). If the second measured value $Z_1$ is lower than the third setpoint $Setpoint_3$, then the HF current remains switched on and the second measured value $Z_2$ for the impedance of the electrode 70, 71 connected to the selected output 15 is measured again (at block S8) by the second measurement device 10 until such time as the second measured value $Z_2$ is greater than or equal to the third setpoint $Setpoint_3$.

If the third comparator 55 establishes that the second measured value $Z_2$ is equal to or greater than the third setpoint $Setpoint_3$, then the third comparator 55 switches off the HF current via a connecting line 67 (block S10) and switches off the second measurement device 10 via a connecting line 56 (block S11) and switches on the first measurement devices 5 for the outputs 15. The circuit 1 of the HF surgical device is again restored to its basic state.

When the electrode 70, 71 contacts biological tissue, the impedance of the electrode 70, 71 is reduced compared to the impedance when there is no contact between the electrode 70, 71 and biological tissue. As long as the electrode 70, 71 remains in contact with the biological tissue, then the HF current will remain switched on. Once there is no longer any contact between the electrode 70, 71 and biological tissue, then the impedance will rise and will be above the third setpoint $Setpoint_3$, leading to the switching-off of the HF current and to the restoration of the circuit 1 of the HF surgical device to its basic state.

The third setpoint $Setpoint_3$ and the fourth setpoint $Setpoint_4$ can have the same value. As a result, the threshold at which the circuit 1 of the HF surgical device is restored to its basic state is the same, irrespective of whether the second measured value $Z_2$ was ever lower than the second setpoint $Setpoint_2$ or not.

Figure 3:
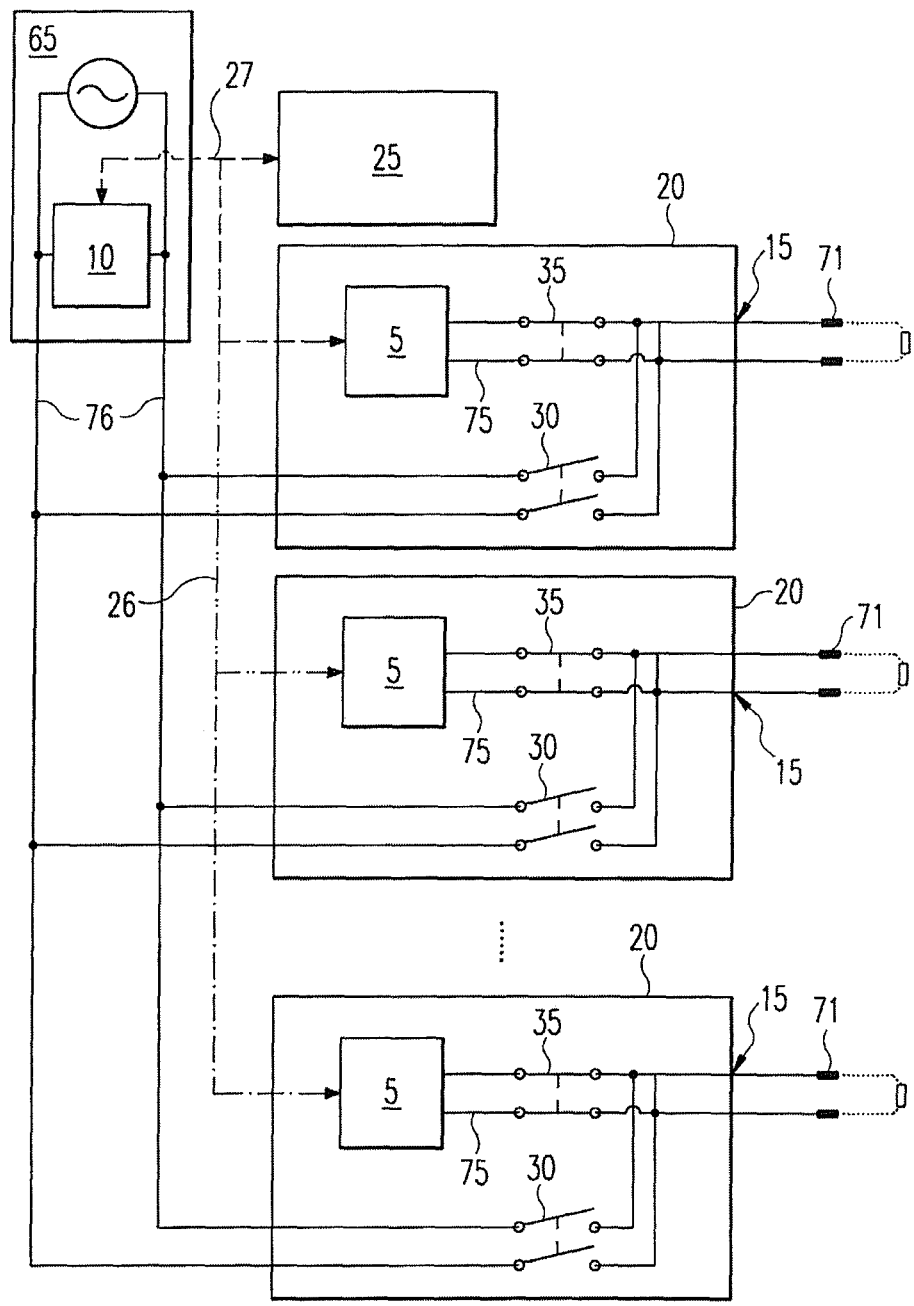
FIG. 3 is a schematic view of a circuit for a HF surgical device during measurement of the impedance by the first measurement devices.
Figure 4:
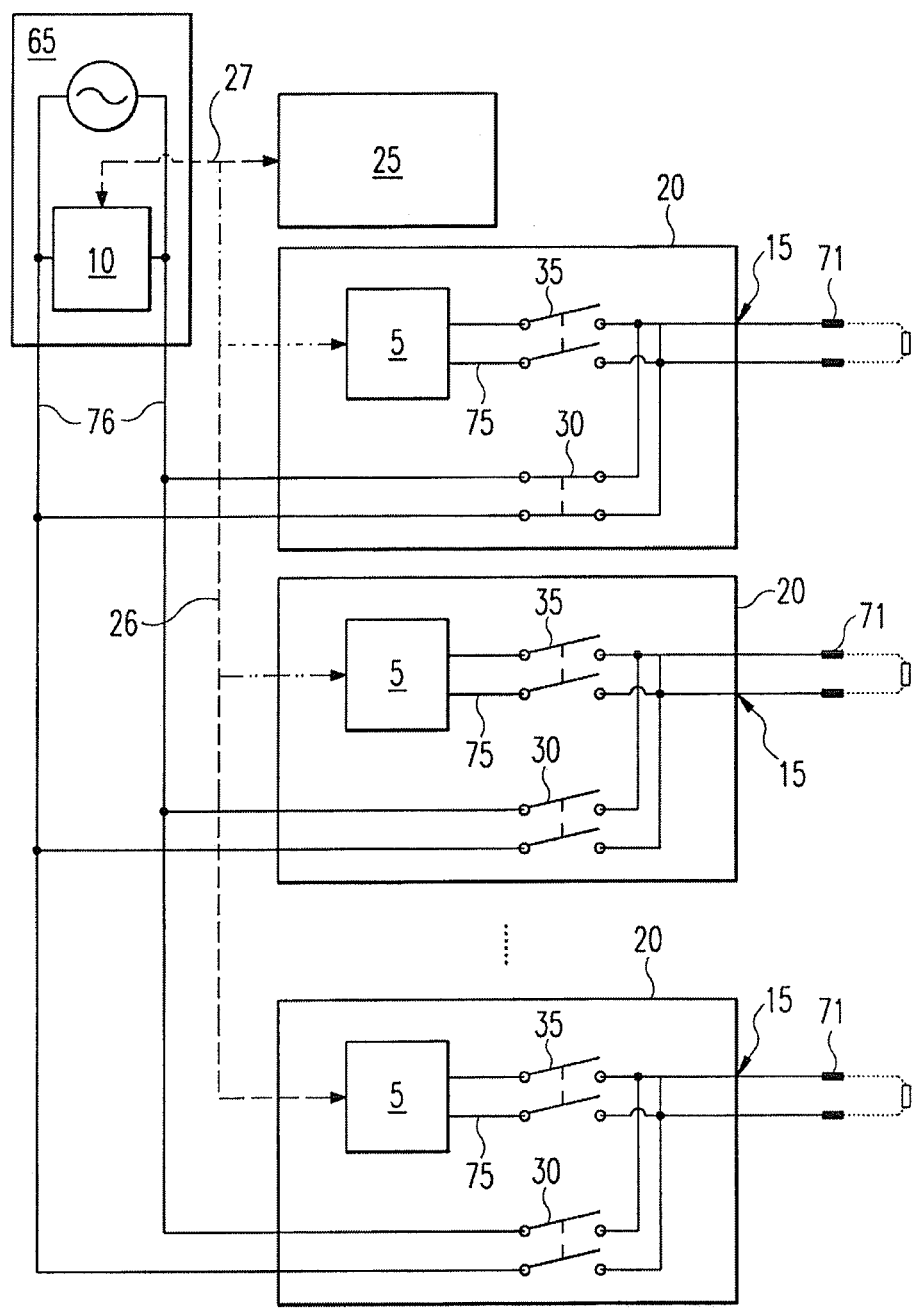
FIG. 4 is the circuit of FIG. 3 during measurement of impedance with the second measurement device/with the HF current switched on, and FIG. 5 is a flow diagram for operation of the circuit according to FIGS. 3/4.

FIG. 3 and FIG. 4 show a schematic view of a circuit 1 of an HF surgical device. The circuit 1 comprises an HF generator 65 for generating the HF current, a control device 25, first measurement devices 5, a second measurement device 10 and a plurality of outputs 15, each for a bipolar electrode 71. The second measurement device 10 is arranged in the HF generator 65. The second measurement device 10 additionally monitors the operating data of the HF generator 65. An output unit 20 is assigned to each output 15 and comprises the respective first measurement device 5, a respective HF relay 30 and a respective measurement relay 35. The first measurement devices 5 are connectable via connecting lines 75 and via a measurement relay 35 to the outputs 15. The HF generator 65 or the second measurement device 5 is connectable via connecting lines 76 and via an HF relay 30 to the outputs 15.

In FIG. 3, the measurement relays 35 are closed, i.e., the first measurement devices 5 are connected to the output 15 for measurement of the impedance of the electrode 71 connected to the respective output 15, i.e., the impedance between the poles of the respective output 15. If the first measured value measured by the first measurement devices 5 is below a first setpoint, then the output 15 corresponding to the earliest-in-time of the first measured values lying below the second setpoint is selected by the control device 25, which is connected via a connecting line 26 to the first measurement devices 5.

As shown in FIG. 4, the first measurement devices 5 are switched off by the control device 25 through opening of the measurement relays 35. The HF relay 30 is closed by the control device 25, which is connected via a connecting line 27 to the second measurement device 10, for the selected output 15, so that the second measurement device 10 and the HF generator 65 are connected to the selected output 15. The second measurement device 10 determines a second measured value for the impedance of the electrode 71 connected to the selected output 15. If the second measured value lies below a second setpoint, then the HF current is switched on for the selected output. While the HF current is switched on, the second measured value is measured again and compared to a third setpoint. As soon as the second measured value is above the third setpoint, i.e., the electrode 71 is no longer in contact with tissue, or the impedance of the tissue has increased as a result of ongoing coagulation, the HF current is switched off, the second measurement device 10 is switched off by opening of the HF relay 30, and the first measurement devices 5 are switched on again by closing of the measurement relays 35.

Figure 5:
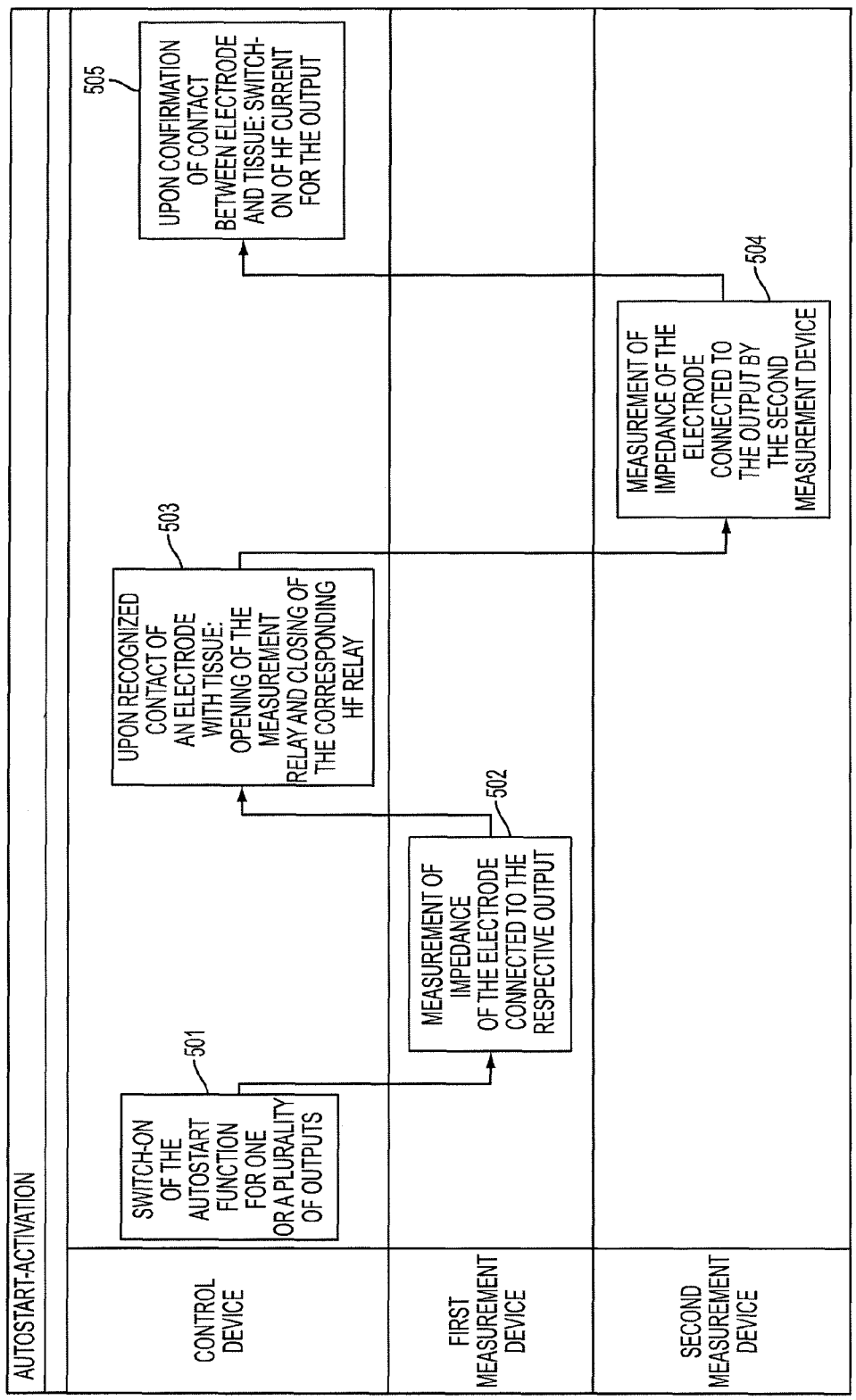

FIG. 5 shows a flow diagram for operation of the circuit 1 according to FIG. 3 or 4. The control device switches on the autostart function for one or a plurality of outputs 15 (block 501). The first measurement devices 5 measure the impedance of the electrode 70, 71 connected to the respective output 15 (block 502). If contact is established between an electrode and tissue, then the control device 25 opens the measurement relay 35 and closes the HF relay 30 for the output 15 corresponding to the first-in-time contact with a value below a setpoint for the impedance (block 503). The second measurement device 10 again measures the impedance of the electrode 70, 71 connected to the output 15 by the HF relay 35 (block 504). If the control device 25 confirms that the electrode 70, 71 contacts tissue by a comparison of the second measured value with a second setpoint, then the HF current is switched on for the electrode 70, 71 (block 505).

It is pointed out here that all of the parts described above are substantial for the embodiments of the invention, either individually or in combination, and in particular, the details shown in the drawings. A person skilled in the art will be familiar with departures here from.

The invention claimed is:

1. An HF surgical device with an autostart function for cutting and/or coagulating biological tissue with HF current, said HF surgical device comprising:
   an HF generator for generating the HF current;
   a selected output for connecting a monopolar or bipolar electrode to the HF surgical device;
   a first measurement device associated with the output and for measuring a first measured value for an impedance of the electrode connected to the output;
   a first comparator for comparing the first measured value to a first setpoint, for switching-off the first measurement device and for switching-on a second measurement device if the first measured value is lower than the first setpoint, and for measuring a second measured value for the impedance of the connected electrode; and
   a second comparator for comparing the second measured value to a second setpoint and for switching-on of the HF current for the output if the second measured value is lower than the second setpoint.

2. The HF surgical device according to claim 1, wherein the second measurement device determines a more precise measured value for the impedance of the electrode connected to the selected output than the first measurement device.

3. The HF surgical device according to claim 1, wherein the first measurement device uses a lower voltage to measure the impedance than a voltage used by the second measurement device.

4. The HF surgical device according to claim 1, further comprising:
   a third comparator for comparing the second measured value to a third setpoint and for switching-off the HF current and the second measurement device and for switching-on of the first measurement device if the second measured value is greater than or equal to the third setpoint.

5. The HF surgical device according to claim 4, further comprising a fourth comparator for comparing the second measured value to a fourth setpoint and for switching-off the second measurement device and for switching-on the first measurement device if the second measured value is greater than or equal to the fourth setpoint.

6. The HF surgical device according to claim 5, wherein the third and fourth setpoints have the same value.

7. The HF surgical device according to claim 1, further comprising a plurality of first measurement devices connected to the output, wherein the first measurement devices are designed such that they measure the first measured values at time intervals disjoint to one another.

8. The HF surgical device according to claim 1, wherein the second measurement device is arranged in the HF generator.

9. An HF surgical device with an autostart function for cutting and/or coagulating biological tissue with HF current, said HF surgical device comprising:
   an HF generator for generating the HF current;
   at least two connections for the connection of monopolar and/or bipolar electrodes to the HF surgical device;
   first measurement devices associated with the respective output for measuring a first measured value for an impedance of the respective electrode connected to the output;
   a first comparator for comparing the first measured values to a first setpoint and for selecting an output corresponding to an earliest-in-time first measured value that is lower than the first setpoint, for switching-off the first measurement devices and for switching-on a second measurement device for measuring a second measured value for the impedance for the electrode connected to the selected input; and
   a second comparator for comparing the second measured value to a second setpoint and for switching-on the HF current for the selected output if the second measured value is lower than the second setpoint.

10. The HF surgical device according to claim 9, wherein the second measurement device determines a more precise measured value for the impedance of the electrode connected to the selected output than the respective first measurement device.

11. The HF surgical device according to claim 9, wherein the first measurement devices use a lower voltage to measure the impedance than a voltage used by the second measurement device.

12. The HF surgical device according to claim 9, further comprising:
    a third comparator for comparing the second measured value to a third setpoint and for switching-off the HF current and the second measurement device and for switching-on the first measurement devices if the second measured value is greater than or equal to the third setpoint.

13. The HF surgical device according to claim 12, further comprising a fourth comparator for comparing the second measured value to a fourth setpoint and for switching-off the second measurement device and for switching-on of the first measurement devices if the second measured value is greater than or equal to the fourth setpoint.

14. The HF surgical device according to claim 13, wherein the third and fourth setpoints have the same value.

15. The HF surgical device according to claim 9, wherein the first measurement devices are designed such that they measure the first measured values at time intervals disjoint to one another.

16. The HF surgical device according to claim 9, wherein the second measurement device is arranged in the HF generator for generating the HF current.

17. A method of automatically starting an HF current of an HF surgical device for cutting and/or coagulating biological tissue with a selected output for a monopolar and/or bipolar electrode, said method comprising:
    switching-on a first measurement device associated with the selected output;
    measuring, by the first measurement device, a first measured value for an impedance of the electrode connected to the output;
    comparing the first measured value to a previously determined first setpoint;
    switching-off the first measurement device and switching-on a second measurement device for the output if the first measured value is lower than the previously determined first setpoint;
    measuring, by the second measurement device, a second measured value for the impedance of the electrode;
    comparing the second measured value to a second setpoint; and
    switching-on the HF current for the output if the second measured value is lower than the second setpoint.

18. The method according to claim 17, wherein the measured value for the impedance is determined more precisely by the second measurement device than by the first measurement device.

19. The method according to claim 17, wherein measurement of the impedance with the first measurement device is carried out at a lower voltage than measurement with the second measurement device.

20. The method according to claim 17, further comprising switching-off the HF current and the second measurement device and switching-on the first measurement device if the second measured value is greater than or equal to a previously determined third setpoint.

21. The method according to claim 20, further comprising measuring again the second measured value for the electrode connected to the output by the second measurement device if the second measured value is lower than the third setpoint.

22. The method according to claim 20, further comprising measuring again the second measured value for the electrode connected to the selected output with the second measurement device if the second measured value is greater than or equal to the second setpoint and lower than a fourth setpoint.

23. The method according to claim 22, further comprising switching-off the second measurement device and switching-on the first measurement device if the second measured value is greater than or equal to the fourth setpoint.

24. The method according to claim 20, wherein the third and fourth setpoints have the same value.

25. The method according to claim 17, wherein there are a plurality of first measurement devices connected to the output and the first measured value is measured at time intervals that are disjoint to one another.

26. A method for automatically starting an HF current of an HF surgical device for cutting and/or coagulating biological tissue with at least two connections for a monopolar and/or bipolar electrode, said method comprising:
   switching-on first measurement devices assigned to the respective output;
   measuring, using the first measurement devices, a respective first measured value for an impedance of the electrode connected to the corresponding output;
   comparing the respective first measured value to a previously determined first setpoint;
   selecting an output corresponding to an earliest-in-time first measured values that is lower than the previously determined first setpoint;
   switching-off the first measurement devices and switching-on a second measurement device for the selected output;
   measuring, by the second measurement device, a second measured value for the impedance of the electrode;
   comparing the second measured value to a second setpoint; and
   switching-on the HF current for the selected output if the second measured value is lower than the previously determined second setpoint.

27. The method according to claim 26, wherein the measured value for the impedance is determined more precisely by the second measurement device than by the respective first measurement device.

28. The method according to claim 26, wherein measurement of the impedance with the first measurement device is carried out at a lower voltage than measurement with the second measurement device.

29. The method according to claim 26, further comprising switching-off the HF current and the second measurement device and switching-on the first measurement devices if the second measured value is greater than or equal to a previously determined third setpoint.

30. The method according to claim 29, further comprising measuring again the second measured value for the electrode connected to the output by the second measurement device if the second measured value is lower than the third setpoint.

31. The method according to claim 29, further comprising measuring again the second measured value for the electrode connected to the selected output with the second measurement device if the second measured value is greater than or equal to the second setpoint and lower than a fourth setpoint.

32. The method according to claim 31, further comprising switching-off the second measurement device and switching-on the first measurement devices if the second measured value is greater than or equal to the fourth setpoint.

33. The method according to claim 30, wherein the third and fourth setpoints have the same value.

34. The method according to claim 26, wherein the first measured value is measured at time intervals that are disjoint to one another.

* * * * *